United States Patent [19]

Alcala

[11] Patent Number: 5,151,869
[45] Date of Patent: Sep. 29, 1992

[54] FREQUENCY DOMAIN FLUOROMETRY USING COHERENT SAMPLING

[75] Inventor: J. Ricardo Alcala, Chatham, N.J.
[73] Assignee: The BOC Group, Inc., New Providence, N.J.
[21] Appl. No.: 481,406
[22] Filed: Feb. 16, 1990
[51] Int. Cl.$^5$ .................... G06G 7/58; G01N 21/64
[52] U.S. Cl. .................... 364/497; 250/458.1; 356/317
[58] Field of Search ............ 364/497, 498, 178, 179, 364/484, 485; 356/317, 318, 417; 250/458.1, 459.1, 461.1

[56] References Cited

U.S. PATENT DOCUMENTS

| | | | |
|---|---|---|---|
| 4,031,398 | 6/1977 | Callis et al. | 250/458.1 |
| 4,365,153 | 12/1982 | Seigel et al. | 250/459.1 X |
| 4,461,572 | 7/1984 | Tsuchiya | 356/318 |
| 4,678,917 | 7/1987 | Helms et al. | 250/461.1 X |
| 4,691,110 | 9/1987 | Nebe et al. | 250/458.1 |
| 4,808,828 | 2/1989 | Kitamori et al. | 250/458.1 |
| 4,840,485 | 6/1989 | Gratton | 356/317 |
| 4,877,965 | 10/1989 | Dandliker et al. | 250/458.1 |
| 4,895,156 | 1/1990 | Schulze | 128/634 |
| 4,937,457 | 6/1990 | Mitchell | 250/458.1 |
| 4,946,279 | 8/1990 | Ohkubo | 356/318 |
| 4,957,366 | 9/1990 | Koshi et al. | 356/318 |
| 5,023,804 | 6/1991 | Hoult | 364/498 |
| 5,053,626 | 10/1991 | Tillotson | 250/458.1 |

OTHER PUBLICATIONS

Feddersen, et al., "Digital Parallel Acquisition in Frequency Domain Fluorometry", Rev. Sci. Instrum. 60 (9), Sep., 1989.
Gratton, et al., "A Continuously Variable Frequency Cross-Correlation Phase Fluorometer with Picosecond Resolution", University of Illinois at Urbana-Champaigh Publication P-83-6-80.
Laws, et al., "Synchrotron Radiation as an Excitation Source in Time-Domain and Frequency-Domain Fluorometry", SPIE, vol. 909 (1988), pp. 23-28.
Bright, "Remote Sensing Technique with a Multifrequency Phase-Modulation Fluorometer", SPIE, vol. 909, pp. 23-28.
Quinn, et al., "A Deconvolution Technique for Determining the Intrinsic Fluorescence Decay Lifetimes of Crude Oils", Applied Spectroscopy, vol. 42, No. 3, 1988, pp. 406-410.
Lakowicz, et al., "Gigahertz Frequency-Domain Fluorometry: Applications to Picosecond Processes and Future Developments," SPIE, vol. 909 (1988), pp. 15-22.
Bright, et al., "A New Frequency-Domain Fluorometer for Rapid Determination of Pico Second Rotational-Correlation Time", J. Applied Physics, vol. 61, pp. 3526-3529 (1987).
Lakowicz, et al., "-GHz Frequency-Domain Fluorometer," Rev. Sci. Instrum., vol. 57, pp. 2499-2506 (Oct., 1986).
Feddersen, et al., "Direct Waveform Collection and Analysis of Phase-Fluorometry Data," Biophysical Journal, vol. 53, No. 2, p. 404A.

*Primary Examiner*—Parshotam S. Lall
*Assistant Examiner*—Collin W. Park
*Attorney, Agent, or Firm*—Roger M. Rathbun; Larry R. Cassett

[57] ABSTRACT

Apparatus and methods for measuring response of a chemical composition to light, as by frequency domain, phase angle, or modulation fluorometry and/or phosphorimetry. Pulsed light having a known fundamental frequency is applied to the composition thereby eliciting response light varying at the fundamental frequency and at harmonics thereof. The response light signal may be sampled according to a wave-skipping sampling scheme, and the sampled response signal may be transformed into a frequency domain representation, as by a digital fast Fourier transform technique. A reference signal derived from the excitation light may be similarly processed and the results used as a basis for comparison to derive properties of the chemical composition such as phase and modulation response of the composition to the fundamental and harmonic frequencies. The invention provides rapid monitoring and determination of luminescence characteristics. Multiple excitation frequencies may be applied simultaneously and the resulting response signals may be separated and separately sampled.

36 Claims, 6 Drawing Sheets

FREQUENCY DOMAIN FLUOROMETRY USING COHERENT SAMPLING

BACKGROUND OF THE INVENTION

Certain chemical compositions exhibit luminescence. Such compositions emit light during exposure of the composition to externally applied light, or for a brief time after the exposure ends. The light emitted by the composition progressively decreases in intensity after the exposure to incoming light ends. Luminescent behavior of this nature includes the phenomena commonly referred to as "phosphorescence" or "fluorescence." It has long been known that significant information concerning the physical and chemical properties of a composition can be deduced from the luminescent behavior as by observing the rate of decay of the emitted light. However, real chemical compositions of interest normally exhibit a plurality of different decay rates which may entail decay times ranging from seconds to picoseconds. With very shortlived luminescence, it is normally not practical to obtain useful information about such compositions simply by exposing the composition to light, terminating the exposure and observing the decay of luminescence.

However, it is possible to obtain equivalent information by exposing the composition to excitation light having amplitude varying at a predetermined frequency and observing the luminescent response of the composition. Typically, the response includes a component varying in intensity at the same frequency as the excitation light. One characteristic of the emitted light which can be observed is the degree of modulation at the particular frequency used, i.e., the ratio between the intensity of the component at this frequency and the total intensity of the emitted light. Another characteristic of the emitted light which can be observed is the phase relationship between the cyclic variations in the emitted light and the variations in the excitation light, i.e., the degree to which variations in the emitted light lag behind variations in the excitation light. It has been the practice heretofore to conduct experiments of this nature at numerous frequencies and gather information such as degree of modulation, phase angle and the like at each such frequency. Utilizing known techniques, significant information concerning the physical and chemical characteristics of the composition can be deduced from the information gathered using plural frequencies.

Typically, the various frequencies of excitation light have been applied to the composition in sequence, one frequency at a time. Such sequential application of the various frequencies may be performed using an automated "scanning. Instrument arranged to apply the various frequencies in a predetermined sequence. Substantial time is required to collect data for all of the various frequencies. This approach is unsuitable for application in dynamic systems where the composition is changing with time. Accordingly, there have been attempts made to obtain similar information by applying light at various frequencies simultaneously and then measuring the response at all of these various frequencies simultaneously. In such simultaneous arrangements, the light emitted by the composition necessarily includes components at the various excitation frequencies employed, which components are intermingled with one another. It has been suggested that these components can be segregated from one another using a multichannel "parallel hardware" structure. In this approach, the instrument would necessarily include a number of signal channels at least equal to the number of frequencies to be monitored. Each such channel would include elements such as filters or the like arranged to limit the response of that particular signal channel to a particular one of the frequencies employed. This approach, however, suffers from serious disadvantages in that the instrument is necessarily limited to operation at only a few frequencies simultaneously. Accordingly, this approach has not been widely adopted.

Another multifrequency instrument is described in Bright et al., "A New Frequency-domain Fluorometer for the Rapid Determination of Picosecond Rotational-correlation Time", *J. Applied Physics*, Vol. 61, pp. 8–11 (January, 1987) and in Bright et al. "Rapid-scanning Frequencies-Domain Fluorometer with Picosecond Time Resolution, *Applied Optics*, Vol. 26, pp. 3526–3529 (1987). In this approach, a sample of the composition is excited with a stream of pulses from a laser operating at a predetermined pulse frequency. According to known principles of mathematics, excitation light varying in such a repetitive pulsatile fashion includes components varying at the fundamental or pulse frequency and also includes further components varying at integral multiples of the fundamental frequency, i.e., at harmonics of the pulse frequency. The light emitted from the sample will likewise include components at all of these frequencies. An additional modulation device may be used to further modulate the excitation light at additional frequencies and thus introduce additional frequencies into the emitted light. The emitted light is converted to an electrical response signal by a photo-multiplier tube, and the resulting electrical response signal is passed to a high frequency spectrum analyzer. The spectrum analyzer provides separate indications of the strength or modulation of the response signal at each frequency corresponding to one or another of the harmonic or additional frequencies. Although an instrument of this type is capable of acquiring data over a wide range of frequencies for a given sample in only about ten seconds or less, it suffers from a fundamental drawback in that it does not provide phase information at any of these frequencies.

Another approach is disclosed by Lakowicz et al., .Two-GHz Frequency-Domain Fluorometer," *Rev. Sci. Instrum.*, Vol. 57, pp. 2499–2506 (October, 1986). The instrument disclosed by Lakowicz et al. also uses a pulsed laser to provide repetitive, pulsatile, excitation light incorporating many harmonics of the pulse frequency This instrument further incorporates a frequency synthesizer for generating a cross-correlation signal at a frequency equal to the frequency of a selected harmonic plus a small offset or delta frequency, typically 25 Hz. The light emitted from the sample is converted to an electrical response signal by a photodetector and the resulting electrical signal is mixed with the cross-correlation signal. This mixing yields an output signal at the same offset or delta frequency containing the phase and modulation information present in the component of the response signal at the selected harmonic A portion of a pulsatile excitation light is diverted prior to reaching the sample and directed to a photodetector to provide a reference signal, which is likewise mixed with the same cross-correlation frequency to provide a reference signal at the same offset or delta frequency. The phase angle for the selected harmonic is obtained by comparing the phasing of the reference and response signals at the offset or delta frequency, whereas the degree of modulation is obtained by comparing the modulation of the reference and response signals. This procedure is repeated using different cross-correlation signals, each at a frequency equal to a different selected harmonic plus the offset or delta frequency, so as to collect a complete set of information incorporating phase angle and degree of demodulation at all different harmonics. Although this instrument exposes the sample to light modulated at many different frequencies simultaneously and provides a signal incorporating the response of the sample at all of the frequencies, the cross-correlation operation is still performed for only one such frequency at a time. Therefore, considerable time is consumed in a measurement. In this respect, the instrument disclosed by Lakowicz et al. suffers from the same drawback as the instrument applying individual excitation frequencies sequentially to the sample.

An abstract entitled "Direct Waveform Collection and Analysis of Phase Fluorometry Data" by Feddersen et al. appearing in the February, 1988 issue of *Biophysical Journal* (Vol. 53, No. 2, page 404a) proposes to digitize the cross-correlated response signal at the offset or delta frequency and likewise to digitize the excitation and reference signals at the offset or delta frequency in an instrument of the type proposed by Lakowicz et al. This is said to facilitate combination of all the data for all of the different harmonics in a global analysis "incorporating data at all of the various frequencies. The abstract states that such digitization "will prove to be very useful" in analysis of signals in some future "parallel fluorometer, where the digitized waveform will simultaneously contain all of the harmonic frequency content of the excitation source."

Accordingly, there have been unmet needs heretofore for still further improvements in instruments and techniques for monitoring the luminescent response of chemical compositions.

SUMMARY OF THE INVENTION

The present invention addresses these needs.

One aspect of the present invention provides improved apparatus for determining the response of a chemical composition to light. The apparatus includes excitation means for producing excitation light varying repetitively in amplitude such that the excitation light includes a fundamental component varying at a fundamental frequency $F_e$ and fundamental repetition period $T_e$ and such that the excitation light also includes harmonic components varying at harmonic frequencies which are integral multiples of $F_e$. The excitation means is arranged to apply the excitation light to the composition. Accordingly, the composition will emit light varying repetitively in amplitude at the fundamental frequency $F_e$ and at the frequencies of the harmonics included in the excitation light. The apparatus according to this aspect of the invention desirably also includes response sampling means for sampling the amplitude of light emitted by the composition repetitively at a sampling frequency $F_s$ and sampling period $T_s$ such that:

$$T_s = T_e N_w + T_e/N_p$$

where $N_w$ is a positive integer and where $N_p$ is a rational number, desirably an integer. Most preferably, the response sampling means is arranged to sample the response signal directly, without cross-correlation or frequency shifting prior to sampling. The response sampling means is arranged to provide the samples as a response series of sample values, most preferably digital sample values, representing the amplitude of the light emitted by the composition. The response samples thus represent a sampled response signal corresponding to the variations in amplitude of the emitted light. The apparatus further includes means for determining at least one characteristic of the sampled response signal.

As explained below, such sampling is a coherent wave-skipping technique. Each sample taken by the response sampling means represents a point on one cycle of the fundamental component in the emitted light waveform. Each succeeding sample is taken on a different cycle of the fundamental, but at a point along the waveform offset by a predetermined delay time from the point where the preceding sample was taken. With sampling according to the aforementioned formula, this delay time is equal to the fundamental repetition period $T_e$ of the emitted light divided by a rational number, $N_p$. Thus, after $N_p$ samples have been taken, the next sample is taken on another cycle but at the same point within the cycle where the first sample was taken. After $N_p$ samples have been taken, the entire sampling pattern repeats itself. This coherent wave-skipping sampling utilizes a relatively low sampling frequency $F_s$, lower than the fundamental repetition frequency $F_e$. However it achieves the same effect as would be achieved by sampling the emitted light many times within each cycle. In effect, the coherent wave-skipping sampling technique causes the sampling device to simulate a sampling device operating at a sampling rate many times higher than the actual sampling rate. The series of samples represents the fundamental and harmonic components in the emitted light up to a predetermined highest harmonic with sufficient accuracy that the amplitude and phase of each of these components can be accurately recovered from the samples. Thus, the apparatus according to this aspect of the present invention can acquire full amplitude or degree of modulation data and full phase data concerning the emitted light at numerous frequencies simultaneously. The instrument according to this aspect of the invention can acquire such data at relatively high harmonic frequencies, far higher than the maximum actual sampling frequency of the sampling device. Preferred apparatus according to this aspect of the present invention can provide amplitude and phase data for frequencies in the gigahertz range using conventional sampling equipment capable of sampling rates of only a few megahertz.

In a variant of this approach, a sampling frequency $F_s$ which is less than the excitation frequency but which does not conform to the aforementioned specific relationship may be employed. Thus, the sampling is asynchronous with the response waveforms. In this variant, the sampling point does not fall on the same portion of the response waveform after some predetermined number of cycles, and hence additional signal processing may be required to extract the data as further discussed below. The asynchronous wave-skipping action provided by this sampling technique is similar to the coherent wave-skipping techniques discussed above. Here, again, a sampling and digitizing device operating at a relatively low repetition rate effectively simulates the action of a device operating at a high repetition rate.

The excitation means typically includes means for providing excitation light as a series of repetitive pulses at a pulse repetition frequency equal to the aforementioned fundamental frequency $F_e$. These pulses include both the fundamental component and the aforementioned harmonics. The response sampling means may include means for providing a repetitive trigger signal at a repetition rate equal to the sampling frequency $F_s$, detector means for providing a continuous electrical signal directly related to the amplitude of the emitted light and triggerable analog to digital conversion means for digitizing the instantaneous value of the electrical signal upon each repetition of the triggering signal.

Preferably, the apparatus also includes means for providing a reference signal having at least one characteristic representing a corresponding characteristic of the excitation light. The means for determining at least one characteristic of the sampled response signal preferably includes means for comparing a characteristic of the sampled response signal with the corresponding characteristic of the reference signal. Thus, the reference signal may be provided in a predetermined phase relationship to the excitation light, and the comparing means may be arranged to compare the phase of the transformed test signal with the phase of the reference signal. The means for providing a reference signal may include means for sampling the excitation light at the sampling frequency $F_s$ so as to provide an excitation series of excitation sample values representing a sampled excitation signal. This sampled excitation signal may be supplied as the reference signal. As with the response signal, the individual components in the excitation signal can be segregated by known mathematical processing techniques. Characteristics of individual components in the sampled response signal, such as degree of modulation, phase and the like may be compared to the characteristics of the corresponding component in the sampled excitation signal at the same frequency.

Apparatus in accordance with a further aspect of the invention also includes excitation means for producing excitation light varying repetitively in amplitude, and including a fundamental component varying at a fundamental frequency $F_e$ and also including harmonic components varying at frequencies which are multiples of $F_e$ and applying the excitation light to the composition. Apparatus according to this aspect of the invention incorporates sampling means for sampling the amplitude of the light emitted by the composition to thereby provide a response series of sample values representing this amplitude, such that the response series of sample values constitute a sampled response signal corresponding to the variations in amplitude of the emitted light. Apparatus according to this aspect of the present invention includes means for transforming the sampled response signal into a frequency domain representation thereof, such that the frequency domain representation includes a value for at least one characteristic of each of plural components at plural frequencies. Preferably, the means for transforming the sampled response signal into the frequency domain representation includes means for applying a digital transformation to the response series of sample values, most preferably a digital fast Fourier transform algorithm or other, similar algorithm such as a digital Hadley transform algorithm. Desirably, the means for transforming the sampled response signal are arranged to provide the frequency domain representation such that this representation includes values for modulation, phase, and desirably both, for each component. The apparatus may further include means for deriving decay characteristics of the composition from the component characteristics included in the frequency domain representation, as from the modulation and phase values for the various components.

The apparatus may also include means for sampling the excitation signal to provide a sampled excitation signal, and means for transforming the sampled excitation signal to provide a frequency domain representation thereof. The means for deriving decay characteristics may include means for comparing the frequency domain representation of the sampled response signal with the frequency domain representation of the sampled excitation signal.

This aspect of the invention includes the realization that the component characteristics and particularly the phases of the individual components calculated by transformation into the frequency domain are particularly sensitive to small variations in the decay time characteristics of the response signal. Therefore, even where the response signal is sampled at a relatively low sampling rate, relatively small variations in the decay time of the response signal can be detected. Stated another way, the sampling frequency or sampling rate required to achieve a given resolution or ability to detect small changes in the decay times of the response signal is considerably less if the decay times are computed from the component characteristics in the frequency domain representation than if the decay times are computed directly from sampled signal. In effect, transformation into the frequency domain expands the time scale and reduces the sampling rate required to follow decay curves of a given rate.

As discussed above, the coherent wave-skipping sampling scheme also serves to reduce the required frequency of operation of the sampling device needed to achieve a given time resolution. The most preferred apparatus according to the present invention includes both the coherent wave-skipping sampling means and the frequency domain transformation means. Thus, the frequency domain transformation means is arranged to apply the transformation to the series of samples recovered by the coherent wave-skipping sampling means. The time expansion or reduction in required sampling rate achieved according to both of these features is cumulative, so that the instrument is capable of monitoring extremely rapid decay with a relatively low actual sampling rate, within the capabilities of actual sampling instruments.

Further aspects of the present invention provide methods of determining the response of a chemical composition to light. The preferred methods include the steps of applying excitation light as aforesaid to the composition and sampling the amplitude of the light emitted by the composition. Preferably, the sampling is performed in a wave-skipping fashion, by repetitively sampling at a sampling frequency $F_s$ and sampling period $T_s$ such that $F_s$ is less than the excitation frequency $F_e$ and $T_s$ is greater than the excitation period $T_e$. Most preferably, $T_s = T_e N_w + T_e/N_p$ where $N_w$ is a positive integer and $N_p$ is a rational number having absolute value greater than 1. The sampling step provides a sampled response signal corresponding to the variations in amplitude of light emitted from the composition. The method further includes the step of determining at least one characteristic of the sampled response signal. Most preferably, this determining step includes the step of transforming the sampled response signal into a frequency domain representation of the sampled response signal. The method according to the present invention may include the steps of providing a reference or excitation signal as aforementioned and sampling this signal to provide a sampled excitation signal. The determining step may include the step of comparing the sampled response signal with the sampled excitation signal, as by transforming the sampled excitation signal into a frequency domain representation thereof and comparing characteristics such as modulation and phase for each characteristic in the frequency domain representation of the sampled response signal with the corresponding characteristic of the corresponding component in the frequency domain representation of the sampled excitation signal. These methods provide advantages similar to those discussed above in connection with the apparatus.

Other objects, features and advantages of the present invention will be more readily apparent from the detailed description of the preferred embodiments set forth below, taken in conjunction with the accompanying drawings

DETAILED DESCRIPTION OF THE PREFERRED EMBODIMENTS

Figure 1:
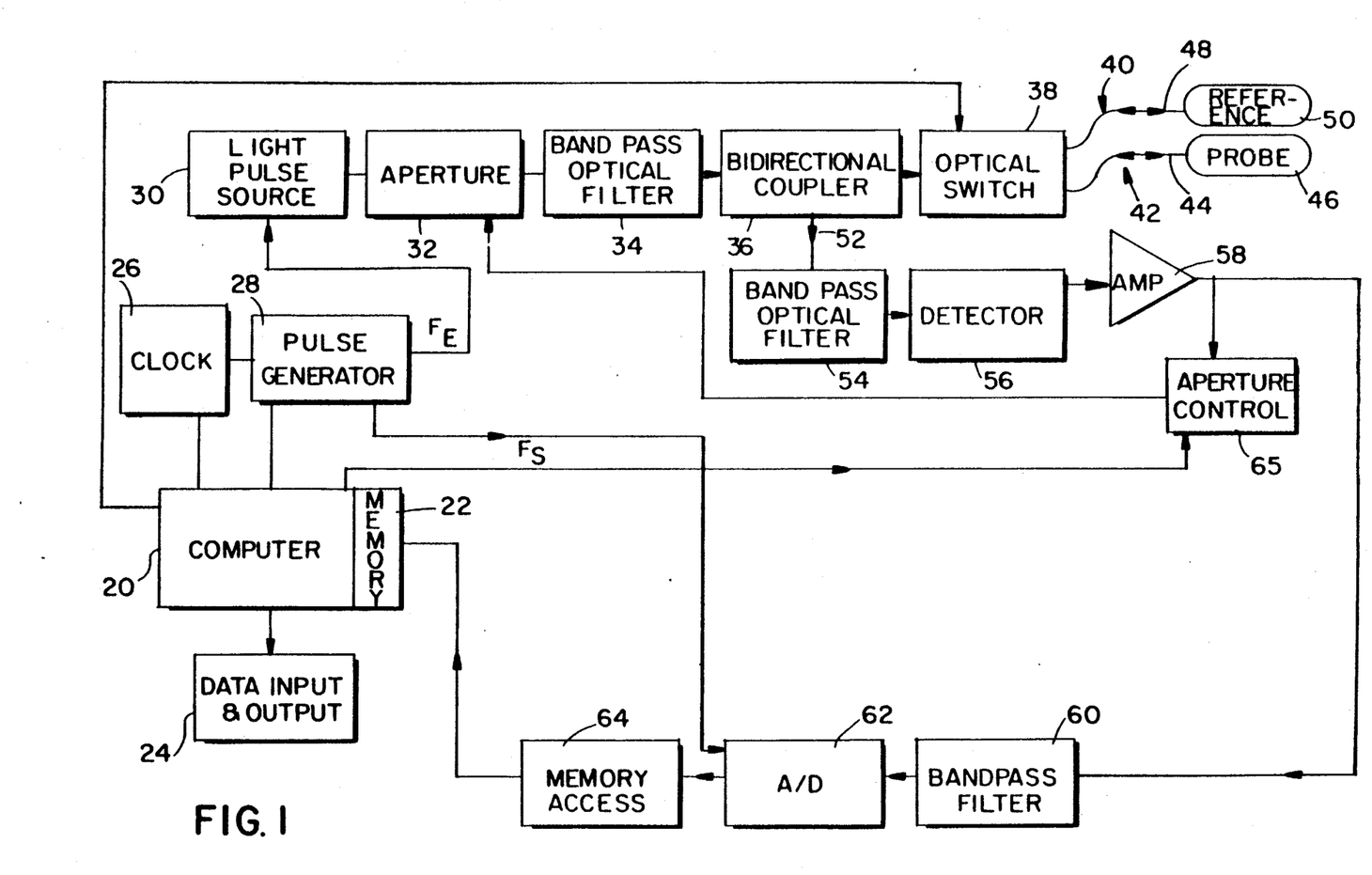
FIG. 1 is a functional block diagram of apparatus in accordance with a first embodiment of the invention.

Apparatus in accordance with one embodiment of the invention incorporates the central control computer 20 having a memory 22 and data input and output devices 24. The apparatus further includes a programmable crystal clock 26 arranged to provide clock pulses at a predetermined frequency. A programmable pulse generator 28 is arranged to provide electrical rectangular wave pulses at an excitation frequency $F_e$ and at a sampling frequency $F_s$ determined by counting clock signals from clock 26. The pulse generator 28 is arranged so that the frequencies $F_e$ and $F_s$ of the rectangular wave pulses can be selected by computer 20, as by adjusting the number of clock signals from clock 26 to be counted off by pulse generator 28 during each cycle. Further, the pulse generator is arranged to vary the breadth or duty cycle of the rectangular wve pulses provided at frequencies $F_3$ and $F_s$ as directed by computer 20.

The output of pulse generator 28 at excitation frequency $F_3$ is linked to the input connection of the light pulse source 30. The light pulse source includes an electrically controllable light emitting structure. This structure may be a device such as a light emitting diode or a combination of elements such as a continuous wave laser coupled to an accousto-optic modulator or other device arranged to control passage of light responsive to applied electrical signals. The light output of pulse source 30 is connected through a controllable variable aperture 32 and a bandpass optical filter 34 to the input of a conventional bi-directional fiber optic coupler 36. Bandpass optical filter 34 is arranged to permit passage of light within a predetermined wavelength band but to block light at wavelengths outside of such band. One output of coupler 36 is connected to an electrically controllable optical switch 38 which in turn is connected to a reference light path 40 and a probe or sample light path 42. The probe light path 42 includes a fiber optic light conducting member 44 and a probe device 46 arranged to direct light from fiber optic 44 into a chemical composition to be studied and to direct light emitted by that chemical composition back along fiber optic 44. For example, probe 46 may include a mass of a resin impregnated with the chemical composition to be studied surrounding the extremity of fiber optical 44. Reference light path 40 incorporates a fiber optic 48 similar to fiber optic 44 and also includes a reference sample 50 of substantially fixed, predetermined properties. The reference light path 40 is arranged so that light directed through fiber optic 48 will pass to the reference sample 50 and then pass back through the fiber optic 48. Reference sample 50 may simply be a mirror or else may be a luminescent composition having substantially fixed properties. In either case, the light emitted back by the reference sample 50 will be a representation of excitation light as applied to the reference sample. Where the reference sample includes a luminescent composition of fixed properties, the representation may include some fixed modification of the excitation light. For example, the light emitted by the reference sample 50 may be delayed in time relative to the excitation light pulses.

Optical switch 38 is linked to computer 20 and is arranged to connect bidirectional coupler 36 either to reference light path 40 or to the sample light path 42. Bidirectional coupler 36 is arranged to direct light from bandpass filter 34 to optical switch 38 and to direct light returned in optical switch 38 through a return output 52 and bandpass optical filter 54 into a detector 56. Detector 56 is arranged to convert light into electrical signals such that the amplitude of the electrical signals is directly related to the amplitude of the incoming light supplied to the detector. Desirably, the detector is a sensitive device having a very fast response time Suitable detectors include photomultiplier tubes such as those supplied under the designation R928 by Hamamatsu Photonics K.K., Hamamatsu, Japan; and include avalanche photodiodes and microchannel plates, also available from the same supplier. The electrical output of detector 56 is connected to an amplifier 58. The output of amplifier 58 is connected to an electrical bandpass filter 60. Bandpass filter 60 desirably has a passband extending from slightly below fundamental excitation frequency $F_e$ to an upper frequency $F_u$ selected as discussed further below $F_u$ typically is about 5 times to about 100 times $F_e$ and preferably about 5 to about 50 times $F_e$. Thus, the passband of filter 60 typically is arranged to encompass fundamental excitation frequency $F_e$ and a predetermined set of harmonics of that frequency such as the fundamental and the first five harmonics, the fundamental and the first 100 harmonics or the like. The output of bandpass filter 60 is connected to the signal input of a triggerable analogue to digital or A/D converter 62. Converter 62 is arranged to capture the instantaneous amplitude of the electrical signal passed through the filter 60 upon receipt of a triggering signal, and to deliver the captured value in digital form. Output of converter 62 is connected through a direct memory access device 64 to the memory 22 of the computer 20, so that digital values supplied by converter 64 can be written into predetermined locations in memory 22 essentially instantaneously without interrupting operation of the processor in computer 20. The trigger input of converter 62 is connected to an output of pulse generator 28 carrying pulses at sampling frequency $F_s$, that each such pulse will trigger converter 62 to capture a further sample.

The electrical output from amplifier 58 is also connected to a feedback aperture control circuit 65. Control circuit 65 is linked to computer 20 so that control circuit 65 can receive a target or set point value for the amplitude of the electrical signal from amplifier 58. Aperture control 65 is also linked to aperture 32, and aperture 32 is responsive to control signals from circuit 65. Thus, the aperture control circuit is arranged to adjust aperture 32 so as to maintain the peak amplitude of the signal from amplifier 58 at the selected set point. Aperture control circuit 65 is also arranged such that it will only adjust the aperture 32 upon appropriate command from computer 20 and, in the absence of such command, aperture control 65 will maintain the setting of aperture 32 at a constant value.

Figure 2:
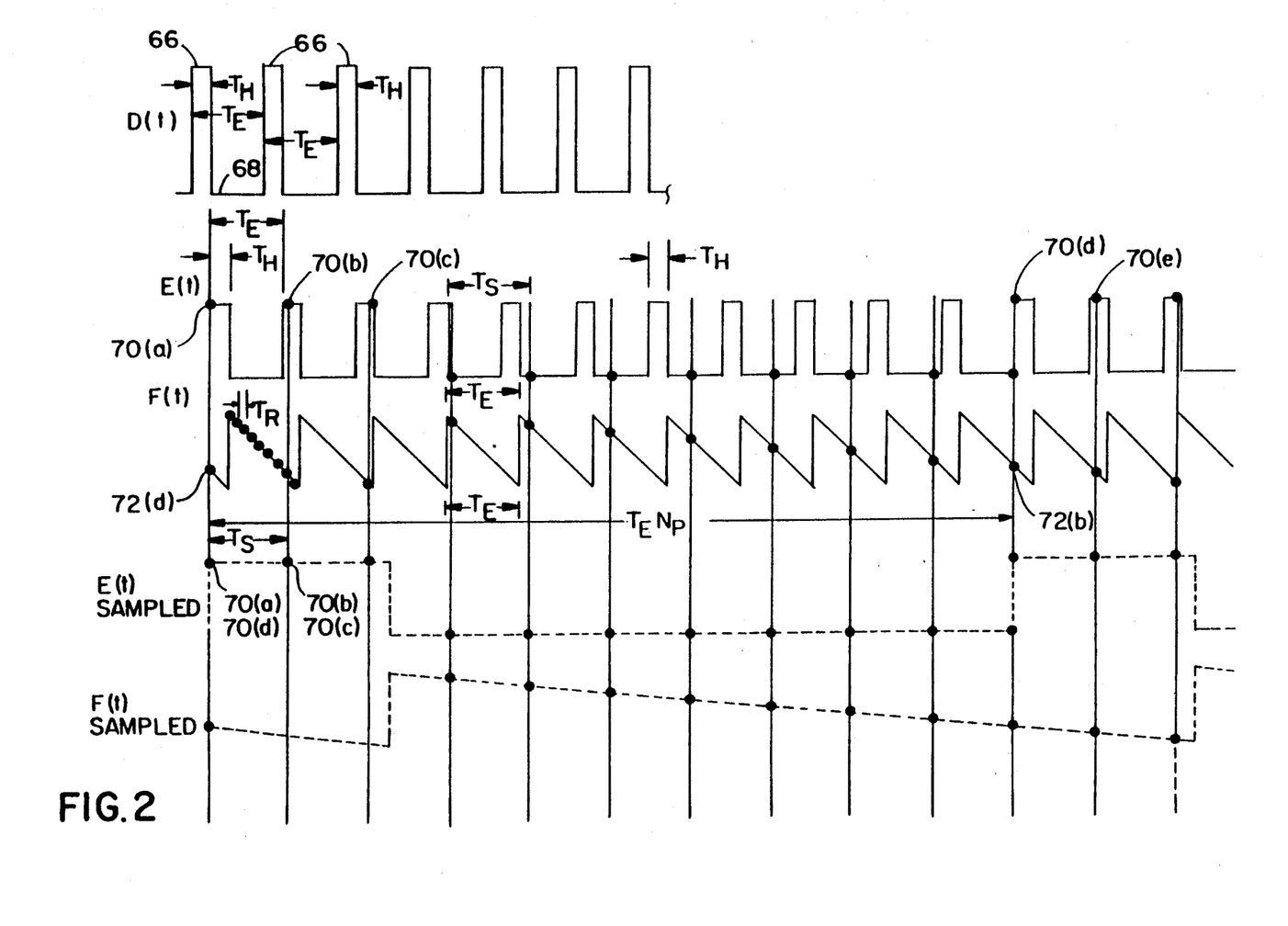
FIG. 2 is an idealized representation of certain waveforms occurring during operation of the apparatus depicted in FIG. 1.
Figure 3:
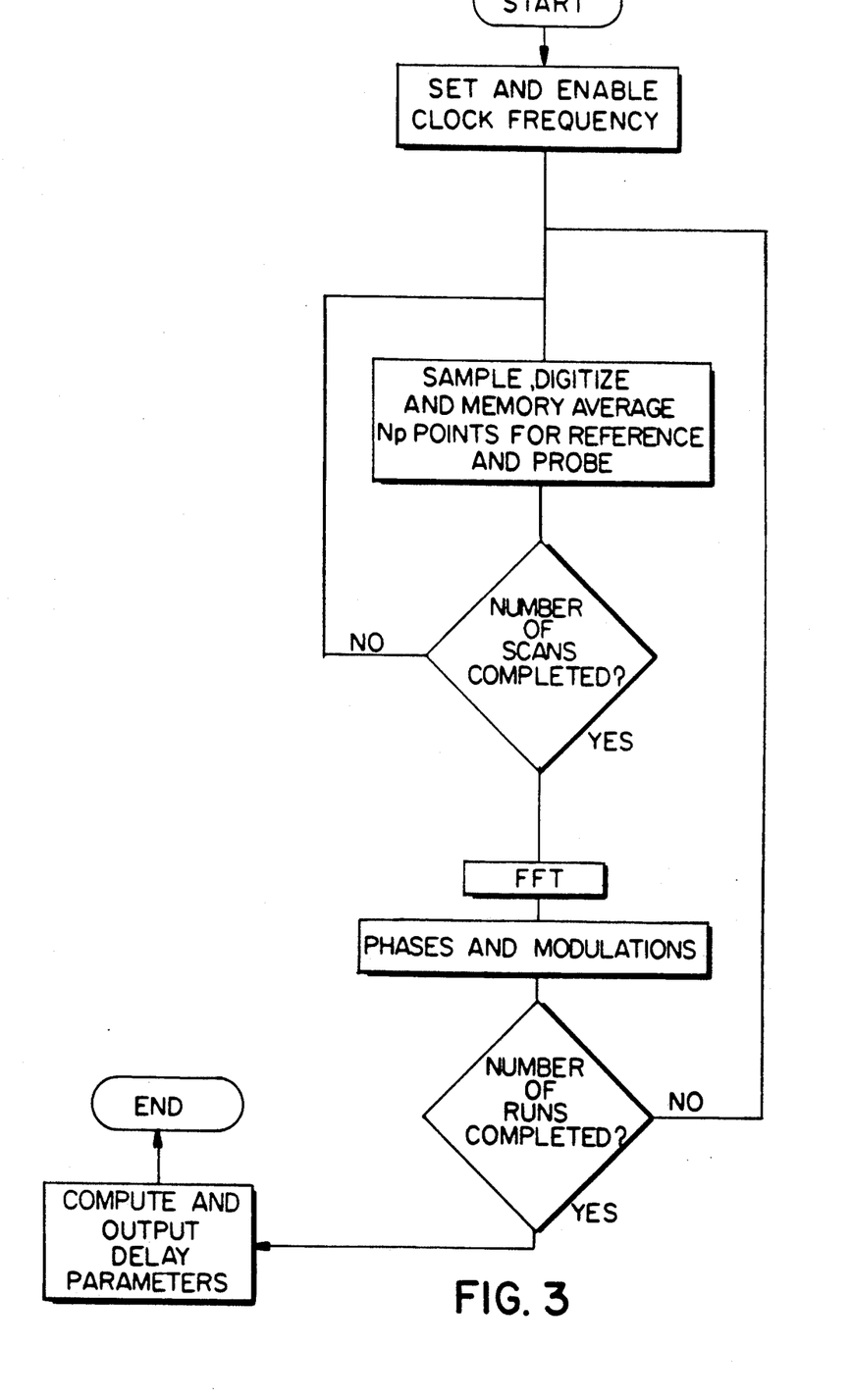
FIG. 3 is a logical flow diagram depicting certain steps in operation of the apparatus shown in FIG. 1.

In a method according to one embodiment of the invention, computer 20 is programmed to actuate the apparatus so as to perform the routine shown in FIG. 3. The computer selects a fundamental frequency $F_e$ to be applied, based upon instructions provided to the computer via data input and output unit 24. Typically, the fundamental frequency $F_e$ used in examination of any particular chemical composition is directly selected by the operator from prior knowledge or assumptions as to the types of luminescent phenomena to be observed and the order of magnitude of the decay times involved. The fundamental frequency of the light pulses applied normally is selected so that the repetition time $T_e$ between succeeding pulses is longer than the decay time of the luminescent phenomena to be observed. Typically, $T_e$ is about 5 times to about 20 times the expected decay time. The computer sets clock 26 to generate clock pulses at a rate substantially higher than the fundamental frequency so selected, and actuates pulse generator 28 to provide a drive signal D(t) series of electrical pulses at the so selected fundamental frequency $F_e$. The computer also controls pulse generator 28 to control the duty cycle of the waveform. As indicated in FIG. 2, the drive signal D(t) alternates between a high state 66 and a low state 68 on each cycle. The time $T_h$ during which the waveform is on or high is a relatively small proportion of the total cycle time $T_e$. The fraction $t_h/T_e$, the proportion of high or on time during each cycle is referred to herein as the "duty cycle" of the wave form. The computer also actuates pulse generator 28 to produce a series of triggering pulses at a sampling frequency $F_s$ and a sampling period $T_s$. As further discussed below, the sampling $T_s$ is selected such that $T_s$ differs slightly from $T_e$, or from some integral multiple of $T_e$. The preferred relationship between $T_s$ and $T_e$ is:

$$T_s = T_e N_w + T_e/N_p \quad \text{(Formula I)}$$

where $N_w$ is a positive integer which may be 1 or greater than 1 and $N_p$ is a rational number having an absolute value greater than 1. Most preferably, $N_p$ is an integer. $N_p$ may be positive or negative.

The drive signal D(t) from pulse generator 28 is applied to light pulse source 30 and the light pulse source provides light varying in amplitude substantially in accordance with this drive signal D(t). Thus, during the high periods 66 of the excitation pulse signal, the light is on, whereas the light is off or at a lower value during the low periods 68. This excitation light passes through aperture 32, bandpass filter 34 and coupler 36 to optical switch 38. Computer 20 initially commands the optical switch to pass the excitation light into reference optical path 40. The reference light is thus along fiber optic 48 into reference sample 50 and light emitted by the reference sample passes back through fiber optic 48 and the switch to coupler 36. This returned reference light passes via optical bandpass filter 54 to detector 56. As the properties of reference light path 48 and of reference sample 50 are substantially fixed, the returned light from the reference path is a representation of the excitation light as the same has been modified by the fixed characteristics of the reference light path a fixed loss of intensity and/or fixed phase delay. Detector 56 provides an electrical signal representing this reference or excitation light impinging on the detector. Aperture control 65 detects the peak amplitude of the signal from amplifier 58 and adjusts the aperture 32 to bring the amplitude of this signal into a specified range, within the operating range of converter 62. Once this adjustment has been accomplished, the aperture control 65 maintains aperture 32 at a constant setting. Bandpass filter 60 provides a filtered version of the electrical signal to A/D converter 62.

The electrical signal passing through bandpass filter 60 during this stage of the method is a reference signal representing the excitation light applied by light pulse source 30 through optical components 30, 34, 36 and 38, and through reference optical path 40, together with any amplitude changes, phase shift or distortion introduced by these components by reference sample 50 or by optical filter 54, detector 56, amplification circuit 58 and filter 60 itself. This excitation signal E(t) (FIG. 2) is substantially in the form of a rectangular wave having the same frequency $F_e$ and repetition period $T_e$ as the original driving signal D(t). Analog to digital converter 62 samples the reference electrical signal passing through filter 60. The reference electrical signal provided by the detector is sampled directly, i.e., without any intermediate cross-correlation, mixing, or frequency-shifting steps. Stated another way, each component of the signal reaching the sampling devices or converter 62 includes the same frequencies as the corresponding component in the signal provided by the detector.

Upon each pulse of the trigger or sampling signal supplied by pulse generator 28, analog to digital converter 62 takes a sample by capturing the amplitude of the reference signal at the instant of the trigger pulse and provides a digital word representing that amplitude. Memory access unit 64 accepts these digital words as the same are generated by analog to digital converter 62 and stores them in order in memory 22. This series of operations continues, so that a reference or excitation series of values is stored in memory 22. Because the repetition period $T_s$ of the sampling or trigger signal applied to A/D converter 62 is slightly different than the repetition period $T_e$ of the excitation signal, each sample captured by A/D converter 62 occurs at a slightly different point in the waveform of the excitation signal E(t). In FIG. 2, the time of each sample is indicated on the E(t) waveform as a black dot. The first such sample 70(a) occurs at the beginning of an "on" or high period. The next sample 70(b) occurs slightly after the beginning of the "on" period during the next cycle of E(t). Sample 70(c) occurs at a slightly later point on the waveform and so on.

In the example depicted in FIG. 2, the sampling period $T_s$ is just slightly more than one $T_e$ of the excitation waveform E(t). That is, $N_w=1$ in the expression $T_s=N_wT_e+T_e/N_p$. Where $N_w$ is greater than one, entire periods of E(t) without samples occur between successive samples. The difference between the time $T_s$ between successive samples and an integral multiple of the period $T_e$ of the excitation waveform is a rational fraction of $T_e$, i.e., $T_e/N_p$ with $N_p$ being a rational number. In the example shown in FIG. 2, $N_p$ is an integer having absolute value greater than one. Therefore, the (Np+1)th sample falls on the same point of the E(t) waveform as the first sample. Thus, sample 70(d) is taken at exactly the same point of the E(t) waveform as sample 70(a). Stated another way, on each sample the sample is delayed relative to the E(t) waveform by $T_e/N_p$, so that after $N_p$ samples have been taken, the accumulated delay of the sample relative to the waveform is equal to $T_e$, i.e., one full repetition period of the waveform, and hence the next sample falls on the same point of the waveform as the first sample. Thus, the sampling is coherent with the excitation waveform. Every $N_p$ samples constitute a complete representation of a single cycle of the waveform. The sampling is continued over a sufficient time to accumulate many times $N_p$ samples.

While the samples are being acquired, computer 20 averages together all of the samples taken from a given point in the waveform. Thus, the computer averages the value recorded at sampling point 70(a), the value recorded at sampling point 70(d) and the value recorded at other sampling points (not shown) at the same point in the waveform, so as to derive an averaged value for all of the samples at this point in the waveform. In like fashion, computer 20 computes an average for all of the samples representing the second point in the waveform, i.e., for sample point 70(b), sample point 70(e) and other, similar values (not shown). Standard computer averaging techniques are used in this stage of the process. Thus, the individual samples are added into $N_p$ running totals maintained in $N_p$ separate memory registers. The computer directs every $(N_p+1)$th sample into the same memory register and the sample is added to the running total in that register. Each total is subsequently divided by the number of samples included in the total. $N_p$ separate averages are computed in this way. These $N_p$ averaged sample values constitute a sampled excitation signal, and collectively represent the complete waveform of the excitation signal E(t). Although the sampling period $T_s$ is actually longer than the repetition period $T_e$ of the waveform, the effective sampling rate is multiplied by a factor approximately equal to the absolute value of $N_wN_p$. Because the waveform is represented by $N_p$ sampled points, the effect is substantially the same as if the sampling rate were about $N_wN_p$ times as great, or as if the fundamental frequency of the excitation waveform E(t) were divided by about $N_wN_p$. This effect is indicated by the hypothetical E(t) sampled waveform depicted in broken lines in FIG. 2. Thus, the interval $T_s$ between successive samples is only a small fraction of the multiplied repetition period of the broken line waveform.

This effect can be explained in terms of sampling theory. Conventional and well-known sampling theory states that with ordinary, non wave-skipping sampling at a sampling rate $F_s$, the samples provide complete information as to the phase and modulation of components in the waveform up to a maximum frequency $F_h$ having fundamental frequency $F_e$, $F_s=N_pF_e$ where $N_p$ is the number of samples per cycle of the waveform. Thus, for ordinary non wave-skipping sampling, $F_h=N_pF_e/2$. The same relationship between $F_h$, $N_p$ and $F_e$ applies to waveskipping sampling. However, with wave-skipping sampling as described above, the relationship between $F_s$ and $F_e$ is different. For coherent wave-skipping sampling: $F_s=N_pF_e/(N_wN_p+1)$. Thus, the relationship between the highest frequency for which information is provided by the samples and the sampling frequency is: $F_h=(N_wN_p+1)F_s/2$. Stated another way, wave-skipping sampling multiplies the maximum frequency $F_h$ observable with a given sampling rate $F_s$ by a factor of about $N_wN_p$.

Conventional, readily available sampling and digitizing equipment such as conventional sample-andhold circuits and analog to digital converters provide a maximum sampling frequency $F_s$ up to about 20 MHz. However, the value of $N_wN_p$ may be up to about several hundred or more. Thus, even with conventional sampling equipment, maximum values of $F_h$ up to several GHz can be obtained. Therefore, the samples can provide complete phase and modulation information for component frequencies from a few hertz to several GHz.

Specialized high rate sampling and digitizing equipment can provide even greater $F_s$ and correspondingly greater $F_h$. Although sampling devices ordinarily are regarded as taking a point sample along a waveform, a real sampling device such as a sample-and-hold circuit actually provides a sample signal representing a portion of the waveform during some small but nonetheless finite sample capture interval. The wave-skipping technique does not appreciably enlarge the allowable sample capture interval. The sample capture interval used in wave-skipping sampling should be no more than the sample capture interval used with ordinary sampling, and desirably should be less than $T_e/N_p$.

To minimize aliasing, the harmonic content of the excitation signal desirably is limited to frequencies of about $F_h$ and below, by selecting the duty cycle of the excitation waveform such that the duty cycle $T_h/T_e$ is less than $1/N_p$. In FIG. 2, $T_h$ is exaggerated relative to $T_e$ for clarity of illustration, and accordingly the duty cycle $T_h/T_e$ should not be inferred from inspection of FIG. 2.

After a predetermined number of samples have been taken with respect to the excitation waveform, computer 20 actuates optical switch 38 to direct the excitation light along the probe optical path 42 rather than the reference path 40, thus staring a test cycle.

During the test cycle, while the repetitive flashes of excitation light are applied to the chemical composition in probe 46, the composition emits light in response to each burst of excitation light, and the intensity of each burst of emitted light decays after the end of a burst of excitation light. The repetitive bursts of emitted light are directed through test or sample optical path 42 and through the optical switch 38, coupler 36 and optical filter 54 into detector 56. The emitted light impinging on detector 56 is converted by the detector and by amplification circuit 58 into an electrical signal, which electrical signal passes through bandpass filter 60. At the beginning of the test cycle, aperture control unit 65 adjusts the aperture 32 so that the light emitted by the chemical composition in probe 46 will produce an electrical signal from amplifier 58 of the appropriate magnitude.

The electrical response signal passing to converter 62 from bandpass filter 60 is depicted schematically as F(t) in FIG. 2. This signal includes a repetitive series of gradual decay periods. As each decay period corresponds to a single excitation light pulse, the response signal F(t) has the same fundamental frequency $F_e$ and the same repetition period $T_e$ as the excitation signal E(t). Analog to digital converter 62 is operated in the same way as discussed above with reference to the excitation signal to take a series of samples of the response signal F(t), using the same sampling frequency $F_s$ and sampling period $T_s$. Here again, the sampling rate is coherent with the fundamental frequency of the waveform, in that the time $T_s$ between samples differs from the nearest integral multiple of the fundamental period $T_e$ of the waveform by a small amount $T_e/N_p$ where $N_p$ is a rational number having an absolute value greater than one. Therefore, after a finite number of fundamental periods or cycles of the waveform, the sample is taken at the same point of the F(t) waveform as previously taken. Most desirably, Np is an integer, so that after $N_p$ samples have been taken, the sampling point falls at the same point in the waveform as previously sampled. Thus, as indicated in FIG. 2, the sampling point 72(b) falls at the same point on the F(t) waveform as sampling point 72(a), taken $t$ samples previously. Here again, the effect is substantially the same as if the sampling rate were about $N_w \cdot N_p$ times higher or as if the frequency of the sampled F(t) were about $N_w N_p$ times lower, as indicated by the waveform F(t) sampled in FIG. 2.

The same increase in maximum observable frequency $F_h$ discussed above with reference to the excitation waveform E(t) also applies in sampling of the response signal F(t). As with the excitation samples, the response samples are captured and stored by memory access unit 64 in memory 22 in sequence, and plural samples representing the same point on the response waveform are averaged by computer 20 to provide an average value for each sampled point on the waveform.

Computer 20 actuates the other components of the apparatus to perform a plurality of reference and test cycles in the manner discussed above, in alternating sequence. The alternating test and reference cycles assure that any drift or variation in the properties of the instrument will be averaged out, and will have equal effects on the response and excitation signals. The data from each cycle (a series of averaged values) is maintained separate in memory 22. Once the required number of cycles has been completed, the computer applies a standard, well-known digital fast Fourier transform algorithm to the data. The individual sampled excitation and reference signals constituted by each series of averaged value stored in memory 22 for each reference cycle and for each test cycle is separately transformed into a Fourier series expansion. The Fourier series expansion $(FS)_r$ of the response signal is given by the expression:

$$(FS)_r = \sum_{n=1}^{n=\frac{N_p}{2}} R_{n,r} \cos(2\pi n f_E t) + I_{n,r} \sin(2\pi n f_E t)$$

where: $R_{n,r}$ is th real magnitude of the response signal component of the $n^{5h}$ harmonic frequency and $I_{n,r}$ is the imaginary magnitude of the response component at the $n^{th}$ harmonic frequency. The Fourier series expansion $(FS)_e$ of the sampled excitation signal is given by an expression of the same format incorporating coefficients $R_{n,e}$ and $I_{n,e}$ representing the real and imaginary magnitudes, respectively, of the excitation signal component at the $n^{th}$ harmonic frequency. The phase delay or difference in phase between the response component at a given frequency and the excitation component at the same frequency is given by the expression;

$$\Delta\phi_\omega(n) = \arctan\left(\frac{I_{n,e}}{R_{n,e}}\right) - \arctan\left(\frac{I_{n,r}}{R_{n,r}}\right)$$

where $\Delta\phi_\omega(\eta)$ is the phase delay for the $n^{th}$ harmonic.

The absolute modulation for each component in the Fourier series expansion of the samples response signal is given by:

$$M_{n,r} = \frac{(R_{n,r}^2 + I_{n,r}^2)^{\frac{1}{2}}}{R_{0,r}}$$

where $R_{0,r}$ is the average intensity or D.C. level of the response signal. Likewise, the absolute modulation of each component in the excitation signal $M_{n,e}$ is given by the same expression but using the coefficients $R_{n,e}$; $I_{n,e}$ and $R_{0,e}$. Using these absolute modulations, the modulation ratio $M_n$ for the nth harmonic frequency is given by $$M_n = \frac{M_{n,r}}{M_{n,e}}$$

The modulation ratio for each component is a measure of the change in modulation at a given frequency.

The computation of each phase delay and of each modulation ratio $M_n$ involves comparison between characteristics of a characteristic of a given $n^{th}$ harmonic component in the Fourier series expansion of the sampled excitation waveform from one reference cycle with the corresponding characteristic of the component in the Fourier series expansion of the sampled response waveform from one test cycle. This comparison effectively removes instrumental effects. Both the excitation and response waveforms incorporate any distortion or phase delay caused by the instrument components. Because the reference optical path 40 and the test or sample optical path 42 are constructed to have substantially the same properties except for the optical properties of the sample, any effects of these paths are also cancelled out by the comparison procedure. Once the phase delay and the modulation ratio have been computed separately for each test cycle, each of these parameters is averaged over all test cycles providing final average values for each parameter.

Because the Fourier series expansion incorporates waveform components at plural harmonics of the fundamental excitation frequency $F_e$, the instrument and the method discussed above effectively obtains information concerning the optical properties of the chemical composition at numerous frequencies in a single operation. Computer 20 may directly output the calculated phase delays and modulation ratios for the various frequencies. Alternatively, computer 20 may calculate luminescence parameters of the chemical composition from these phase delays and modulation ratios. The relationships employed to translate phase delays and modulation ratios at plural frequencies into an expression I(t) relating luminescent decay to time are known. Among the relationships which may be used are the following:

$$\tan(\Delta\phi_n) = \frac{S(nf_E)}{G(nf_E)}$$

$$M_n = \frac{1}{N} [S^2(nf_E) + G^2(nf_E)]^{\frac{1}{2}}$$

where $$S(nf_E) = \int_0^\infty I(t) \sin(2\pi nf_E t)\, dt$$

$$G(nf_E) = \int_0^\infty I(t) \cos(2\pi nf_E t)\, dt$$

$$N = \int_0^\infty I(t)\, dt$$

These relationships are applied by assuming a functional form for I(t) such as a superposition of plural discrete or exponential decays; a superposition of continuous exponential decays in terms of lifetime distributions or probability density functions or a superposition of first and second order decays.

Determination of the decay characteristic I(t) from a frequency domain representation such as the Fourier series expansions discussed above provides a significantly enhanced resolution of short-time events in the decay. The time resolution for the frequency domain representation of a given sampled signal is substantially better than the time resolution which could be achieved by direct observation of the sampled signal itself. Stated another way, to measure an event having a given time span tau, such as a lifetime, of an excited state contributing to luminescence, a system employing a direct observation of the sampled waveform would require that times between samples be approximately equal to tau. However, when the frequency domain representation is observed the time between samples may be an order of magnitude greater than tau, and typically about 20(pi)(-tau). In effect, the excitation and sampling rates may be relatively low when the frequency domain representation is employed.

In the system described above, both the wave-skipping sampling technique and the use of the frequency domain representation allow the instrument to detect very brief events having a small tau. Where the events to be measured are relatively slow, with a substantial value of tau, one of these approaches may be omitted. Thus, standard sampling techniques may be employed instead of the wave-skipping sampling techniques discussed above. The computer 20 simply sets $F_s$ such that: $F_s = N_p F_e$, i.e., $N_w = 0$ in the expressions discussed above.

The methods and apparatus discussed above can acquire information covering a wide range of decay signal components at frequencies ranging from a few Hz to GHz, and hence can acquire information about decay characteristics occurring over ranges of time from seconds to picoseconds. However, gathering such a broad range of information using only a single excitation signal would require a relatively low frequency excitation signal, with a sampling rate sufficient to encompass many harmonics of that low frequency fundamental. This would imply a Fourier series expansion including hundreds or even thousands of terms. Such a large Fourier series expansion requires substantial computational effort and requires either a large, expensive computer or substantial computing time. Moreover, the excitation and response signals must incorporate all of the various components to be monitored. The bandpass electrical filter 60 must be set to admit signals over a broad frequency range. This in turn increases the noise content of the signals presented to analog to digital converter 62.

To avoid difficulties of this nature, a plurality of separate excitation signals at widely differing fundamental frequencies $F_e$ may be employed. In one such method, the apparatus discussed above can be actuated to apply excitation pulses of different fundamental frequencies at different times. During each such operation, bandpass electrical filter 60 is adjusted to pass signal components at the fundamental frequency applied and to pass a reasonable number of harmonics. Typically, the bandpass filter is set to accommodate a range of frequencies from the fundamental frequency applied to an upper frequency less than the maximum frequency $F_h$ set by sampling considerations as discussed above. The upper frequency may be about 5 times to about 100 times the fundamental, and preferably about 5 times to about 50 times the fundamental. The operations discussed above are performed, and then repeated once again with a new fundamental frequency, typically several orders of magnitude different from the first-applied fundamental frequency. Filter 60 may be a parameteric or switchable filter which can be automatically adjusted by computer 20 when a new fundamental frequency is employed. In each case, the bandpass filter is set to a relatively narrow range, and hence can reject most of the noise in the electrical signal from amplifier 58. The information gathered using each fundamental frequency provides information about decay characteristics of the luminescence on a different time scale. For example, information gathered using a fundamental frequency on the order of a few hertz will provide information about decay characteristics over a time span of seconds to milliseconds, whereas information gathered using a fundamental excitation frequency in the KHz range provides luminescence information in the millisecond to microsecond range and so on. The frequency ranges monitored for the different excitation frequencies need not overlap one another.

Although use of plural excitation frequencies in sequence in this manner does require repetition of the experiment a few times to gather complete information about the luminescence characteristics of the composition, it should be clearly appreciated that the number of repetitions required to gather complete information is many times less than the number of repetitions required to gather equivalent information by monitoring only one frequency at a time. On each repetition of the method in accordance with this aspect of the invention, an entire range of frequencies is monitored. Also, such repetition is only employed if characteristics on widely varying time scales must be monitored.

Figure 6:
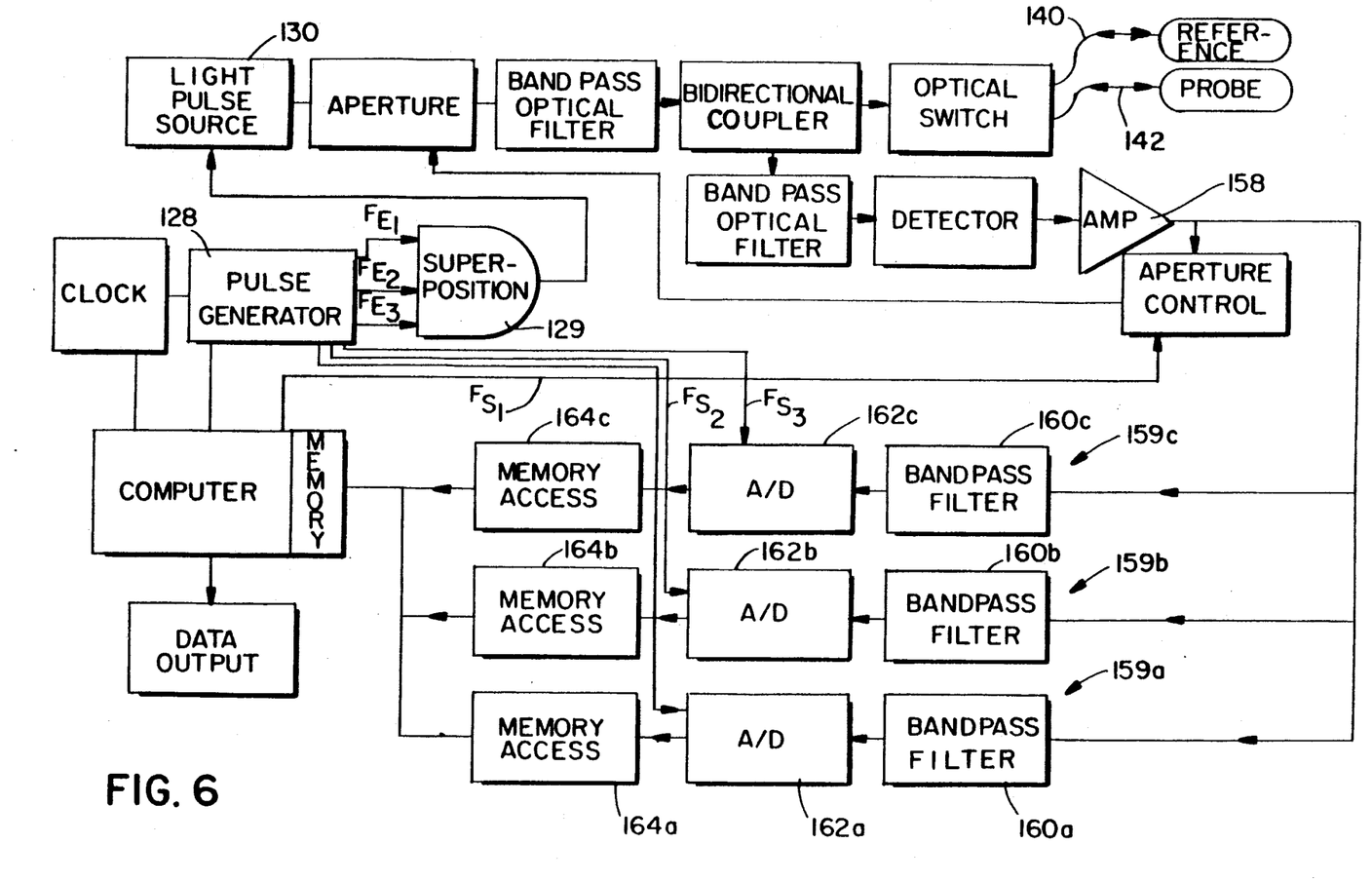
FIG. 6 is a functional block diagram similar to FIG. 1 but depicting apparatus according to a further embodiment of the invention.

Even these few repetitions may be dispensed with by applying excitation light at a plurality of fundamental frequencies simultaneously and simultaneously sampling the response resulting from each such separate excitation frequency. Apparatus in accordance with FIG. 6 can be used for this purpose. The apparatus of FIG. 6 is substantially identical to the apparatus discussed above with reference to FIGS. 1-3 except that the pulse generator 128 is arranged to generate drive signal pulses at a plurality of separate excitation frequencies $F_{e1}$; $F_{e2}$; $F_{e3}$, and also to generate a plurality of sampling pulse signals at a plurality of sampling frequencies $F_{s1}$; $F_{s2}$ and $F_{s3}$, each associated with one of the fundamental excitation frequencies. The relationship between each sampling frequency and the associated fundamental excitation frequency is the same as the relationship between fundamental excitation and sample frequencies discussed above. Pulse generator 128 is connected to a superposition circuit 129 arranged to merge the separate drive signals at the separate excitation frequencies into a single drive signal by multiplying the drive signals by one another, or else by adding the drive signals to one another. The output of superposition circuit 129 is connected to the light pulse source 130.

The apparatus incorporates three separate sampling channels 159. Each sampling channel includes a bandpass filter 160, analog to digital converter 162 and memory access unit 164 similar to the corresponding components of the apparatus discussed above with reference to FIGS. 1-3. The sampling signal at the first sampling frequency $F_{s1}$ is connected to the trigger input of analog to digital converter 162a, whereas the second sampling signal at frequency $F_{s2}$ is connected to the trigger input of converter 162b and the third sampling signal at frequency $F_{s3}$ is connected to the trigger input of converter 162c. Bandpass filter 160a has a pass band including the first excitation frequency $F_{e1}$ and a reasonable range of harmonics thereof, whereas the second bandpass filter 160b is set to pass $F_{e2}$ and some harmonics thereof and the third filter 160c is set to pass $F_{e3}$ and harmonics thereof. Preferably, the three fundamental excitation frequencies $F_{e1}$, $F_{e2}$ and $F_{e3}$ differ from one another by a substantial amount, as by one or more orders of magnitude, and the pass bands of the three filters 160a, 160b and 160c do not overlap. In operation, the composite drive signal applied to light pulse source 130 is applied through the reference optical channel 140 and through the sample optical channel 142 in alternating sequence, in the same manner as discussed above. The light passing back from either optical channel is transformed as discussed above, yielding a composite electrical signal at the output of amplifier 158.

This composite signal will incorporate components at the three fundamental excitation frequencies, and at harmonics of each such frequency. Each bandpass filter effectively selects only those components representing one of the three fundamental frequencies and a reasonable range of its harmonics. Thus, each bandpass filter provides a separate response or excitation signal to the associated analog to digital converter, and each such separate signal is separately sampled. Desirably, the three fundamental excitation frequencies are not integral or rational multiples of one another. Therefore, these three different excitation frequencies will be asynchronous with one another. The sampling of each signal in each of the separate sampling channels is coherent with the associated excitation signal but incoherent with respect to the other excitation signals. Thus, to the extent that $F_{e1}$ or $F_{e2}$, or any harmonics thereof, leak through bend pass filter 160c, they will appear as noise in the signal sampled by converter 162c and will be incoherent with the sampling frequency used. Therefore, any such leakage components will be substantially suppressed by the sampling and averaging process. The same is true of the other channels.

The apparatus and methods discussed above provide data defining the response to light of a chemical composition. As used in this disclosure, the word "light" includes not only visible light but also includes electromagnetic radiation outside of the visible spectrum, such as infrared and ultraviolet radiation. As is well known, the response of a chemical composition to light can provide useful information with respect to the structure of the composition. Also, certain compositions respond differently to light under different conditions. For example, the response of certain compositions changes in repeatable ways as conditions such as temperature and the chemical constitution of the surrounding environment change. Thus, instruments and methods in accordance with the present invention can be used to observe these changes in the environment by monitoring the response of the composition. The probe of the instrument containing the chemical composition to be monitored may be inserted into the environment to be observed. Use of a fiber optic light path is particularly advantageous in this regard, as the probe containing the chemical composition may be a very small element mounted at the tip of a fiber optic. Such a probe can be inserted into an otherwise inaccessible environment, such as into a blood vessel or bodily aperture of a living subject.

In a variant of the wave-skipping sampling discussed above with reference to FIG. 2, the sampling may be performed asynchronously with respect to the excitation or reference signal being sampled, but nonetheless at a sampling frequency lower than the excitation frequency. In this variant, the sampling frequency and sampling period do not conform to the preferred relationship set forth in Formula I, above. Because the sampling frequency is lower than the excitation frequency, successive samples will be taken from different cycles of the waveform. As the sampling frequency differs from the fundamental frequency of the waveform, different samples will be taken at different phases of the waveform, just as in the coherent waveskipping variant discussed above. In the asynchronous system, however, the samples do not fall on the same phase of the waveform after any predetermined number of samples have been taken. Thus, a large number of individual samples, each at a unique phase of the waveform can be collected. This set of unique samples may be processed to provide data essentially equivalent to the data from plural sets of repetition samples discussed above. Although plural unique sample values cannot be directly averaged, the sample values can be processed according to known mathematical techniques to provide a data-smoothing effect similar to averaging. Thus, known linear interpolation techniques can be used to derive quasi-averaged amplitude values for each phase of the waveform from plural amplitude values in samples taken at neighboring phases.

This asynchronous wave-skipping sampling technique may be applied either in the single-channel instrument of FIG. 1 or the multichannel instrument of FIG. 6. In each case, the response or excitation waveform desirably is sampled directly, without any intermediate cross-correlation or frequency shifting stage.

Numerous additional variations and combinations of the features described above can be utilized without departing from the present invention as defined by the claims. Merely by way of example, the magnitude of the output signal from the detector 56 and amplifier 58 may be maintained within desired limits by feedback control of the detector response and/or the amplifier gain, or by feedback control of the intensity of the light pulse source 30, responsive to measurement of the amplifier output. Such feedback control of the pulse source intensity may involve control of the amplitude of the pulses applied by pulse generator 28. The reference signal discussed above, and the use of the sampled reference signal or its frequency domain transformation as a basis for comparison may be omitted. The response signal obtained from the chemical composition to be monitored, or the frequency domain transformation of the response signal, may be observed directly and compared to an assumed or fixed standard. Also, the particular configurations of components can be varied. In the apparatus discussed above, the detector produces a continuous electrical signal representing light incident on the detector, and this signal is sampled discontinuously by one or more analog to digital converters. In an alternate arrangement, the detector may be operated discontinuously, such that the detector is triggered by the sampling trigger signal. Triggerable photomultiplier tubes are well known in the art, and can be used as a detector in such a scheme. Also, the light pulse source may incorporate devices such as light emitting diodes, continuous wave light sources in conjunction with Pockel's cells or an acousto-optic modulator, laser diodes and mode-locked or cavity-dumped lasers. As these and other variations and combinations of the features described above can be utilized without departing from the invention as defined by the claims, the foregoing description of the preferred embodiments should be taken by way of illustration rather than by way of limitation of the present invention.

The following non-limiting example is to be understood as merely illustrating certain features of the invention:

EXAMPLE

Figure 4:
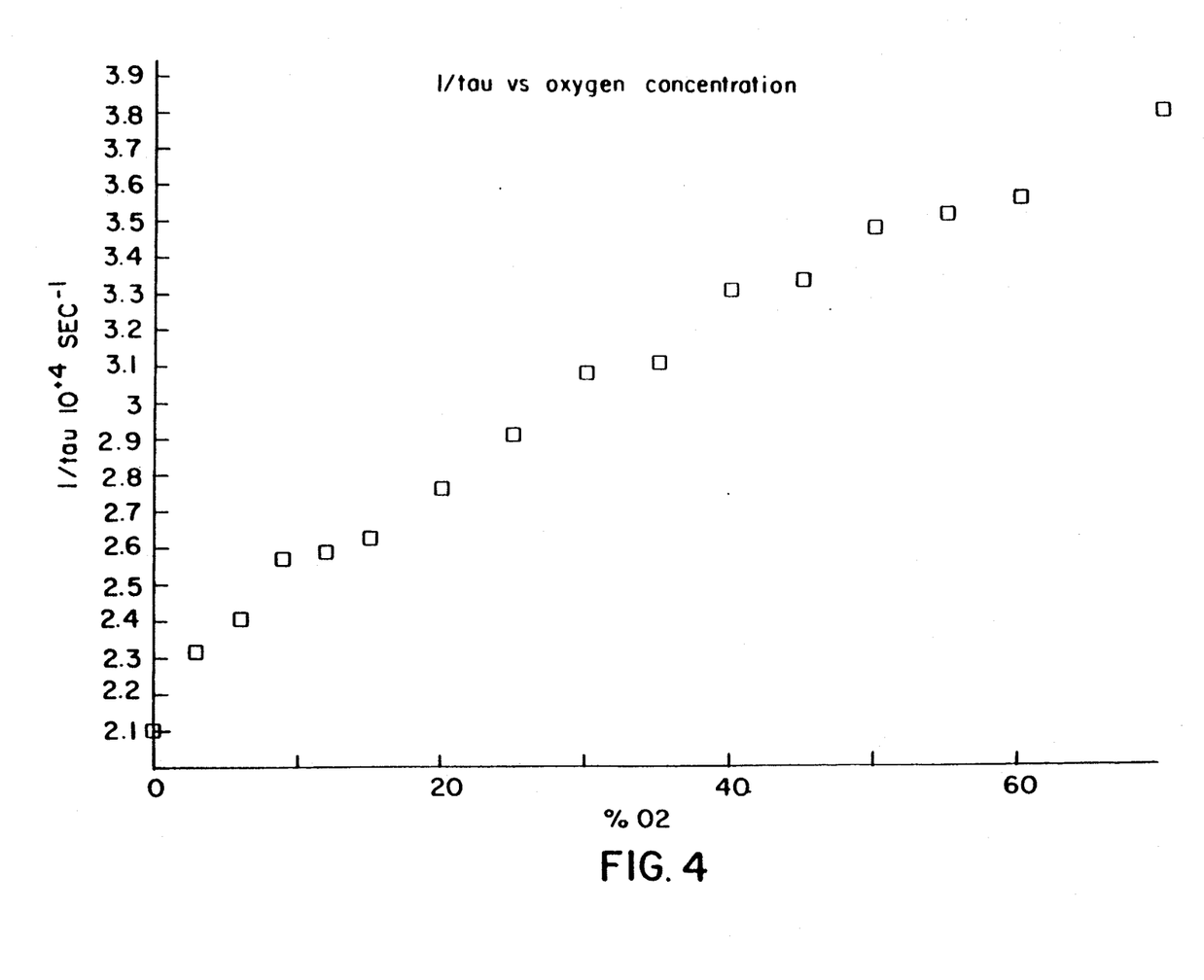
FIGS. 4 and 5 are graphs depicting variations of certain emitted light characteristics under certain operating conditions.
Figure 5:
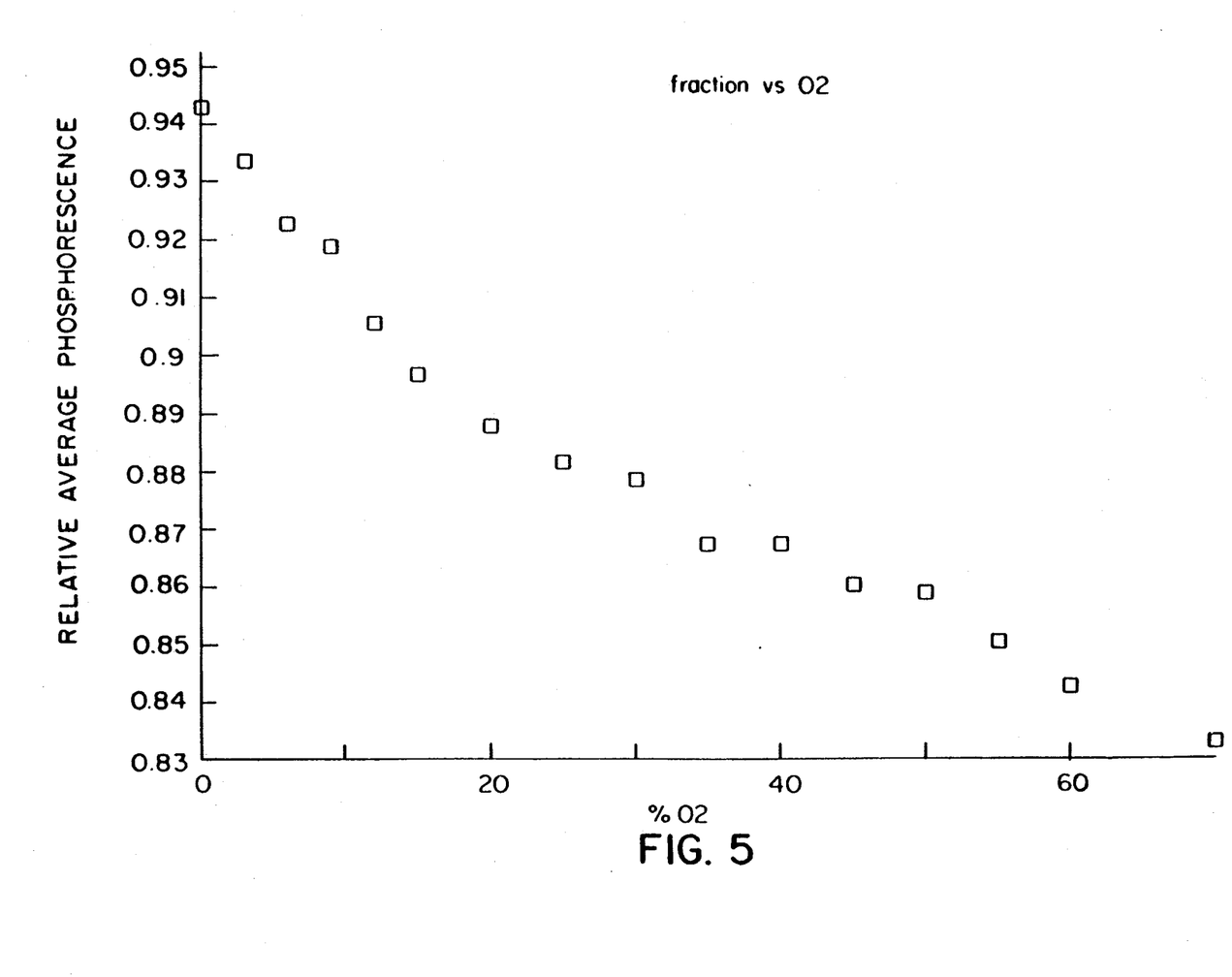

An apparatus generally in accordance with FIG. 1 is employed with a probe 46 incorporating a solution of a platinum porphyrine in a silicone rubber resin. This material phosphoresces during and after application of light. The reference sample is a nonmetal-bearing porphyrine which only fluoresces during application of light. The sample optical path 42 incorporates a 100 micrometer diameter glass optical fiber, and the probe or porphyrine/polycarbonate solution is bonded to the end of this fiber. The probe is immersed in a test gas mixture incorporating oxygen and nitrogen at atmospheric pressure. The excitation light employed has a fundamental pulse frequency $F_e$ of 1.5625 kHz. The sampling frequency is 50 kHz, and hence provides $N_w = 0$ and $N_p = 32$. The samples are taken utilizing an 8;-bit ADC 0820 analog to digital converter available from National Semiconductor Corporation. The detector is a Hamamatsu R-928 photomultiplier tube, providing a response signal with flat frequency response up to frequencies in the MHz range. The output of the detector is filtered by a low-pass filter having a $-3dB$ top cutoff frequency of about 20 kHz. The sampled response and excitation waveforms are averaged 1,000 times in the time domain and 5 times in the frequency domain to give final average modulation and phase data. This data in turn is fitted to a linear single exponential functions I(t) describing the decay time constant 1/tau and also describing the relative average of phosphorescence or magnitude of the sample phosphorescent response. Each such complete measurement, including both excitation signal and test signal acquisition and calculations requires only seven seconds. The measurements are read as the oxygen content of the gas mixture is varied. The results are indicated in FIGS. 4 and 5. The values of 1/tau and of relative average phosphorescence provide useful measures of the test gas oxygen content.

What is claimed is:

1. Apparatus for determining a response of a chemical composition to light comprising:
    (a) excitation means for producing excitation light having repetitive variations in amplitude, including a fundamental component varying at a fundamental frequency $F_e$ and fundamental repetition period $T_3$ and also including harmonic components varying at harmonic frequencies which are integral multiplies of $F_e$ and applying said excitation light to said composition whereby said composition will emit light having repetitive variations in amplitude at modulation frequencies corresponding to $F_e$ and to said harmonic frequencies;
    (b) sampling means for directly sampling the amplitude of light emitted by said composition repetitively at a sampling frequency $F_s$ and sampling period $T_s$ such that $F_s$ is less than $F_e$ and $T_s$ is greater than $T_e$, and $T_s$ is not an integral multiple of $T_e$ and providing a response series of sample values representing said amplitude of said emitted light, whereby said response series of samples will represent a sampled response signal corresponding to the variations in amplitude of said emitted light at said modulation frequencies and;
    (c) means for determining at least one characteristic of said sampled response signal.

2. Apparatus as claimed in claim 1 wherein said sampling means is operative to sample said response signal so that:

$$T_s T_e N_w + T_e/N_p$$

where $N_w$ is a positive integer and $N_p$ is a rational number having an absolute value greater than one 3. Apparatus as claimed in claim 2, wherein said sampling means is operative at a sampling rate $F_s$ such that $N_p$ is an integer.

4. Apparatus as claimed in claim 2 wherein said sampling means includes detector means for providing a continuous electrical signal directly related to the amplitude of said emitted light, means for providing a repetitive triggering signal at said sampling frequency $F_s$ and analog to digital conversion means for digitizing the instantaneous value of said continuous electrical signal upon each repetition of said triggering signal.

5. Apparatus as claimed in claim 4 further comprising anti aliasing means for excluding from said sampled response signal components having a frequency greater than $F_h$ wherein $F_h = (N_w N_p + 1)F_s/2$, said anti aliasing means including means for low pass filtering said continuous electrical signal.

6. Apparatus as claimed in claim 4 further comprising anti aliasing means for excluding from said sampled response signal components having a frequency higher than $F_h$ wherein $F_h = (NWNp+1)Fs/2$ 7. Apparatus as claimed in claim 2 wherein said sampling means includes means for averaging said sampled response signal over a plurality of cycles of the fundamental component therein.

8. Apparatus as claimed in claim 2 wherein said excitation means includes means for providing excitation light including a plurality of fundamental components varying at a plurality of fundamental frequencies $F_e$ and fundamental repetition periods $T_e$, and further including harmonics of each such fundamental frequency, whereby said modulation frequencies will include each of said fundamental frequencies and harmonicas thereof, and wherein said sampling means includes means for providing a plurality of separate series of sample values by sampling the amplitude of light emitted by said composition separately at each of a plurality of sampling frequencies $F_s$ and sampling periods $T_s$, each said sampling frequency $F_s$ and sampling period $T_s$ being associated with one of said fundamental frequencies and fundamental repetition periods, the relationship between each said sampling period $T_s$ and the associated fundamental repetition period being in accordance with said relationship $$T_s = T_e N_w + T_e/N_p$$

where $N_w$ and $N_p$ for the various fundamental frequencies $F_e$ and sampling frequencies $F_s$ may be the same or different whereby each said separate series of sample values will represent a separate sampled excitation signal corresponding to variations in said emitted light within a separate range of said modulation frequencies incorporating one said fundamental frequency and a preselected number of harmonics of that fundamental frequency.

9. Apparatus as claimed in claim 8 wherein said excitation means includes means for providing said excitation light including all of said fundamental components and all of said harmonics simultaneously.

10. Apparatus as claimed in claim 9 wherein said sampling means includes means for detecting the emitted light and generating a composite analog signal representing variations in said emitted light in all of said ranges of frequencies simultaneously, a plurality of sampling devices, and bandpass filter means for separating components of said composite analog signal in different ones of said ranges of modulation frequencies into separate parts of said composite analog signal and directing different parts of said composite analog signal to different ones of said sampling devices.

11. Apparatus as claimed in claim 1 wherein said excitation means includes means for providing repetitive pulses of light at a pulse repetition frequency equal to said fundamental frequency Fe.

12. Apparatus as claimed in claim 11 wherein said excitation means includes means for controlling said excitation light pulses so that said excitation light pulses have a duty cycle less than or equal to 1/N.

13. Apparatus as claimed in claim 1 further comprising means for providing a reference signal having at least one characteristic representing a corresponding characteristics of said excitation light, said means for determining at least one characteristic of said sampled response signal including means for comparing said at least one characteristic of said sampled response signal with a corresponding characteristic of said reference signal.

14. Apparatus as claimed in claim 13 wherein said means for providing a reference signal includes means for sampling said excitation light at said sampling frequency $F_s$ to thereby provided an excitation series of sample values, whereby said excitation series of sample values will represent a sampled excitation signal corresponding to the variations in amplitude of said excitation light at said modulation frequencies.

15. Apparatus as claimed in claim 14 wherein said means for comparing includes means for determining the degree of modulation for components at each of a plurality of said modulation frequencies in each of said sampled response signal and said sampled excitation signal and comparing the degree of modulation for each component in said sampled response signal with the degree of modulation for a corresponding component at the same modulation frequency in said sampled excitation signal.

16. Apparatus as claimed in claim 14 wherein said means for comparing includes means for determining the phase relationship between each component in said sampled response signal and a corresponding component in said sampled excitation signal at the same modulation frequency.

17. Apparatus as claimed in claim 14, wherein said means for comparing at least one characteristic of said sampled response signal with a corresponding characteristic of said reference signal includes means for transforming said response signal into a frequency domain representation including values of at least one characteristic of each of a plurality of response components at a plurality of said modulation frequencies, means for transforming said sampled excitation signal into a frequency domain representation thereof including values of at least one characteristic for each of a plurality of excitation components at said plurality of modulation frequencies and means for comparing the value of each such characteristic for each such response component with the value of the corresponding characteristic for the corresponding excitation component at the same modulation frequency.

18. Apparatus as claimed in claim 17, wherein said means for transforming said sampled response signal and said means for transforming said sampled excitation signal includes means for providing modulation and phase values of each said response component and for each said excitation component respectively.

19. Apparatus as claimed in claim 17, wherein means for transforming said sampled response signal includes means for applying a digital transformation to said response series of values and said means for transforming said sampled excitation signal includes means for applying a digital transformation to said excitation series of values.

20. Apparatus as claimed in claim 13 wherein said means for providing a reference signal includes means for directing said excitation light through a light path of predetermined characteristics and providing said reference signal representing said excitation light after such passage.

21. Apparatus for determining a response of a chemical composition to light comprising:

(a) excitation for producing excitation light having repetitive variations in amplitude, including a fundamental component varying at a fundamental frequency $F_e$ and fundamental repetition period $T_e$ and also including harmonic components varying at frequencies which are integral multiples of $F_e$ and applying said excitation light to said composition whereby said composition will emit light having repetitive variations in amplitude of said modulation frequencies corresponding to $F_e$ and to said frequencies of said harmonic components;

(b) sampling means for directly sampling the amplitude of light emitted by said composition to thereby provide a response series of samples representing said amplitude of light emitted by said composition, whereby said response series of samples will represent a sampled response signal corresponding to the variations in amplitude of said emitted light at said modulation frequencies;

(c) means for transforming said response series of sample values to a frequency domain representation thereof including value for at least one characteristic of each of plural response components at a plurality of said modulation frequencies by applying a digital transformation to said response series of values; and (d) means for determining a luminescence function of said chemical composition from said characteristics of said response components.

22. Apparatus as claimed in claim 21, wherein said means for transforming said sampled response signal includes means for providing a value of modulation and a value of phase for each said response component.

23. Apparatus as claimed in claim 21, further comprising means for sampling said excitation light at said sampling frequency $F_s$ to thereby provide an excitation series of sample values constituting a sampled excitation signal corresponding to the variations in amplitude of said excitation light at said modulation frequencies and means or transforming said sampled excitation signal into a frequency domain representation thereof including at least one characteristic of each of a plurality of excitation components at a plurality of said modulation frequencies, said means for determining at least one characteristic of each said response component including means for comparing each characteristic of each said response component with the corresponding characteristic of a corresponding one of said excitation components at the same modulation frequency.

24. A method for determining a response of a chemical composition to light comprising the steps of:
(a) exciting said chemical composition with light having repetitive variations in amplitude at a fundamental frequency $F_e$ and fundamental repetition period $T_e$ and also including harmonic components varying in amplitude at frequencies which are integral multiples of $F_e$, whereby said composition will emit light having repetitive variations in amplitude at modulation frequencies corresponding to $F_e$ and to said frequencies of said harmonic components;
(b) directly sampling the amplitude of light emitted by said composition repetitively at a sampling frequency $F_s$ less than $F_e$ and sampling period $T_s$ greater than $T_e$ so as to provide a response series of sample values representing said amplitude, whereby said response series of sample values will constitute a sampled response signal corresponding to the variations in amplitude of said emitted light at said modulation frequencies; and
(d) determining at least one characteristic of said sampled response signal.

25. A method as claimed in claim 24 wherein said sampling step is conducted so that:

$$T_s = T_e N_w + T_e/N_p$$

where $N_w$ is a positive integer and $N_p$ is a rational number having absolute value greater than 1.

26. A method as claimed in claim 25, wherein said sampling step is conducted at a sampling frequency $F_s$ such that $N_p$ is an integer.

27. A method as claimed in claim 25 wherein said sampling step includes the steps of detecting said emitted light and providing a continuous electrical signal directly related to the amplitude of said emitted light, providing a repetitive triggering signal at said sampling frequency $F_s$ and digitizing the instantaneous value of said continuous electrical signal upon each repetition of said triggering signal.

28. A method as claimed in claim 27 wherein said sampling step further includes the step of excluding from said sampled response signal components having a frequency greater than $F_h$ wherein $F_h = (N_w N_p + 1)F_s/2$ by low filtering said continuous electrical signal.

29. A method as claimed in claim 25, wherein said exciting step includes the step of providing excitation light including a plurality of fundamental components varying at a plurality of fundamental components varying at a plurality of fundamental frequencies $F_e$ and fundamental repetition periods $T_e$, and further including harmonics of each such fundamental frequency, whereby said modulation frequencies will include each of said fundamental frequencies and harmonics thereof, and wherein said sampling step includes the step of providing a plurality of separate series of sample values by sampling the amplitude of light emitted by said composition separately at each of a plurality of sampling frequencies $f_s$ and sampling period $T_s$, each said sampling frequency $F_s$ and sampling period $T_s$ being associated with one of said fundamental frequencies and fundamental repetition period, the relationship between each said sampling period $T_s$ and the associated fundamental repetition period being in accordance with said relationship $$T_s = T_e N_w + T_e/N_p$$

whereby each said separate series of sample values will represent a separate sampled excitation signal corresponding to variations in said emitted light within a separate range of said modulation frequencies incorporating one of said fundamental frequencies and a preselected set of harmonics of that fundamental frequency.

30. A method as claimed in claim 24 further comprising the steps of providing a reference signal having at least one characteristic representing a corresponding characteristic of said excitation light, said step of determining at least one characteristic of said sampled response signal including the steps of comparing said at least one characteristic of said sampled response signal with a corresponding characteristic of said reference signal.

31. A method as claimed in claim 30 wherein said step of providing a reference signal includes the step of sampling said excitation light at said sampling frequency $F_s$ to thereby provide an excitation series of sample values, whereby said excitation series of sample values will represent a sampled excitation signal corresponding to the variations in amplitude of said excitation light at said modulation frequencies.

32. A method as claimed in claim 31 wherein said step of comparing at least one characteristic of said sampled response signal with a corresponding characteristic of said reference signal includes the steps of transforming said response signal into a frequency domain representation including values of at least one characteristic of each of a plurality of response components at a plurality of said modulation frequencies, transforming said sampled excitation signal into a frequency domain representation thereof including values of at least one characteristic for each of a plurality of excitation components at a plurality of said modulation frequencies and comparing the value of each such characteristic for each such response component with the value of the corresponding characteristic for the corresponding excitation component at the same modulation frequency.

33. A method as claimed in claim 29, wherein said exciting step includes the step of providing said excitation light including all of said fundamental components and all of said harmonics simultaneously.

34. A method as claimed in claim 33 wherein said sampling step includes the step of detecting the emitted light and generating a composite analog signal representing variations in said emitted light in all of said ranges of modulation frequencies simultaneously, separating components of said composite analog signal in different ones of said ranges of modulation frequencies into separate parts of said composite analog signal and directing said separate parts to different sampling devices.

35. A method of determining a response of a chemical composition to light comprising steps of:
   (a) applying excitation light having repetitive variations in amplitude at a fundamental frequency $F_e$ and fundamental repetition period $T_e$ and also including harmonic components varying at frequencies which are integral multiples of $F_e$ to the composition so that the composition emits light including response components having repetitive variations in amplitude at modulation frequencies corresponding to $F_e$ and to said frequencies of said harmonic components;
   (b) directly sampling the amplitude of light emitted by the composition to thereby provide a response series of sample values representing the amplitude of the emitted light whereby the response series of sample values will constitute a sampled response signal corresponding to the variations in amplitude of the emitted light at said modulation frequencies;
   (c) transforming said sampled response signal to a frequency domain representation thereof including values for at least one characteristic of each of said plurality of response components; and
   (d) determining a luminescence characteristic of said chemical composition from said characteristics of said response components.

36. A method as claimed in claim 35, wherein said step of transforming said sampled response signal is performed by applying a digital transform to said sampled response values.

* * * * *